United States Patent [19]

Tsuru et al.

[11] Patent Number: 5,085,781
[45] Date of Patent: Feb. 4, 1992

[54] SEPARATING AGENT, SEPARATOR AND METHOD OF SEPARATING CELL OR VIRUS

[75] Inventors: Sumiaki Tsuru; Akihiko Yokoo; Takeshi Ichitsuka; Tsuneo Hiraide, all of Tokyo, Japan

[73] Assignee: Asahi Kogaku Kogyo Kabushiki Kaisha, Tokyo, Japan

[21] Appl. No.: 486,220

[22] Filed: Feb. 28, 1990

[30] Foreign Application Priority Data

| Feb. 28, 1989 | [JP] | Japan | 1-48000 |
| Mar. 1, 1989 | [JP] | Japan | 1-49175 |
| Mar. 23, 1989 | [JP] | Japan | 1-71342 |
| Jun. 19, 1989 | [JP] | Japan | 1-156195 |

[51] Int. Cl.$^5$ .................... B01D 15/00; B01D 39/02; B01D 39/14
[52] U.S. Cl. .................... 210/692; 210/290; 210/492; 210/502.1; 210/691; 210/807; 422/101; 436/177; 435/2; 502/402; 502/404
[58] Field of Search .............. 210/660, 679, 690, 807, 210/502.1, 266, 284, 290, 489, 492, 691, 692; 502/402, 404; 422/101; 436/177, 178; 435/2

[56] References Cited

U.S. PATENT DOCUMENTS

| 3,741,388 | 6/1973 | Takahashi | 210/386 |
| 3,838,957 | 10/1974 | Koide et al. | 264/51 |
| 3,951,859 | 4/1976 | Inaba et al. | 502/402 |
| 4,190,576 | 2/1980 | Thompson et al. | 210/663 |
| 4,246,351 | 1/1981 | Miyake et al. | 210/502.1 |
| 4,553,966 | 11/1985 | Korteweg | 604/317 |
| 4,761,366 | 8/1988 | Nakajima et al. | 435/2 |
| 4,781,904 | 11/1988 | Tagaya et al. | 423/308 |
| 4,865,733 | 9/1989 | Tsuru et al. | 210/502.1 |

FOREIGN PATENT DOCUMENTS

| 0252472 | 1/1988 | European Pat. Off. |
| 56-140886 | 11/1981 | Japan |
| 57-204454 | 12/1982 | Japan |
| 61-235752 | 10/1986 | Japan |
| 63-284 | 1/1988 | Japan |
| 63-16045 | 1/1988 | Japan |

OTHER PUBLICATIONS

Tsuru, S. et al., "A rapid method for the isolation of functional human T lymphocytes using hydroxy apatite column fractionation," *Journal of Immunological Methods*, 106:169-174 (1988).

*Primary Examiner*—W. Gary Jones
*Attorney, Agent, or Firm*—Sandler, Greenblum & Bernstein

[57] ABSTRACT

A separating agent which includes a polyvinyl acetal resin having open cell structure and an average pore size of from about 10 to about 1000 micrometers; and, porous calcium phosphate granules having open cell structure, and also having two distributions of pore size wherein one distribution has micropores ranging from about 20 to about 500 nm in average pore size and the other distribution has small pores ranging from about 1 to about 50 micrometers in average pore size. Alternatively, the separating agent includes a polyvinyl acetal resin having open cell structure and having an average pore size of from about 10 to about 1000 micrometers as a first element, and a layer of porous calcium phosphate granules having an average granule size of from about 10 to about 2000 micrometers as a second element applied onto the first element. The separating agents may be used in a separator, and may be employed in separating methods. The separating agents, separator, and separating methods can be advantageously used to isolate a target cell or virus from a biological fluid in the fields of medical science and biochemistry. The distribution of target cell or virus subsets is not altered by the separation.

34 Claims, 3 Drawing Sheets

SEPARATING AGENT, SEPARATOR AND METHOD OF SEPARATING CELL OR VIRUS

BACKGROUND OF THE INVENTION

1. Field of the Invention

The present invention relates to the separation of an animal or plant cell or virus from a biological fluid.

More particularly, the present invention relates to a separating material for use with a cell or virus, a separator for use with the cell or virus, and a method of separating the cell or virus. According to the present invention, the target cell or virus can be separated with high speed, at low cost, providing high and constant recovery or yield and good reproducibility without changing the distribution of target cell subsets. The separating method can be advantageously utilized in various fields, including the medical sciences and biochemistry.

2. Description of Related Art

Recently, in the fields of medical science and biochemistry, attempts have been made to separate or isolate a specific group of cells from a suspension containing several different groups of cells, to conduct a basic evaluation of the substances in clinical testing such as immunodiagnosis or immunotherapy. However, there is no method of rapidly separating the target cells at low cost without altering the distribution of target cell subsets, if it is intended to selectively obtain cells such as T, B, K, or NK cells from lymphocytes. As described below, the prior art methods suffer from a number of problems.

Japanese Unexamined Patent Publication (Kokai) Nos. 56-140886 and 57-204454 each disclose the use of a particulate substance containing an acidic functional group or of a hydrophobic and water-insoluble particulate substance with micropores. According to the methods in these Japanese Kokais, it is possible to obtain T cells in a single separation step, but the amount of recovery of the T cells is inconstant and also at a remarkably reduced level. In addition, clogging of the column is caused by the small particle size of the particulate substance used.

Of course, there are some cell separation materials and methods which are internationally recognized to be useful in the area of academic or scientific studies. However, all of these materials and methods require an extended period of time to complete preliminary arrangements for the separation, careful operation of the separation process, and are time-consuming and troublesome. Moreover, they suffer from insufficient reproducibility, because the separation power and separation pattern of the cell separation material used can vary greatly depending on the specific production lot of the material.

Further, Japanese Kokai No. 61-235752 discloses that hydroxyapatite granules have specific adsorptivity to cells. However, their water retention and, accordingly, separation power is rather poor, while a shortened operation time can be obtained. In contrast, Japanese Kokai No. 63-284 states that as a result of using a fibrous apatite, separation power could be improved together with an improved water retention. However, it should be noted that generally a fibrous filler, including the fibrous apatite of Kokai '284, does not result in a uniformly filled state, when packed in a column, and also cannot provide more stable performances in comparison with granular filler, because the performances can vary greatly with changes in the lot used.

More specifically, a "SEPHADEX G10" cell separation method using dextran is well-known in the field of immunodiagnosis. Although the principles of this method have not been completely clarified, it is considered that the level, i.e., higher or lower, of the adhesion properties of the cells play a leading role in this method. Namely, macrophages or adhesive accessory cells having a large size are separated by adsorption, while T cells and B cells pass through the column. However, it is essential to this method that small non-adsorptive accessory cells pass through the column, and some of the subsets of the T cells adhere to the filler. Because of the undesirable adhesion of the T cells, it is impossible to obtain a complete population of the T cells. These problems must be solved to effectively carry out SEPHADEX G10 method in the immunodiagnosis.

Furthermore, use of a separation column containing a filler of nylon wool is also well-known. This column is generally used to separately obtain T cell-rich cell groups, but the effective recovery or yield of the target T cells is relatively low, in the range of 12 to 25%. Also, while the T cells can be obtained at a relatively high purity, the distribution of the T cell subsets is changed after passing through the column. Namely, the distribution of the separated T cell subsets is not the same as that of the T cell subsets in the starting cell suspension. In addition to this variation of the cell population, the separating power and separation pattern may also vary depending upon various factors such as the specific lot of nylon wool selected, the specific splitting method of the wool, the specific filling method, and the specific washing method, even though the wool is filled in the column after the weighing.

As is appreciated from the above discussion, at present, the cell separation technologies based on the adsorptive properties of the cells are merely at a starting point in terms of practical use. It is therefore desired to improve the cell separation materials and methods and to develop a novel separation material, thereby ensuring high efficiency, speed, and accuracy in separation of the cells. If this improvement and development is attained, the cell separation technologies will be more widely and more advantageously utilized in various important fields such as biotechnology and medical science, for example, in immunodiagnosis and immunotherapy.

In addition to cell separation, an improvement in virus separation is also an important goal in the fields of medical science and biochemistry. Since the virus separation is essential to prophylaxis and treatment of viral diseases including influenza, and recently carriers of acquired immune deficiency syndrome (AIDS) virus are rapidly increasing, improvements in virus separation are particularly of urgent necessity for medical care. At present, particularly with regard to the separation of the hepatitis B virus, several virus separation technologies using a polymeric membrance, hollow fiber, or ion exchange resin are well-known. However, these separation technologies entail complicated operation and expensive separation devices due to the specific separation systems thereof. This is the reason why these technologies have not yet been put to practical use.

As previously discussed, Japanese Kokais Nos. 61-235752 and 63-284 teach the use of hydroxyapatite granules in cell separation, but suffer many drawbacks and do not suggest that their teachings may be applied in virus separation. Moreover, Japanese Unexamined Patent Publication (Kokai) No. 63-16045 discloses porous granules of calcium phosphate as a filler in liquid chromatography. The calcium phosphate granules can be used in the chromatographic column to selectively separate and purify a biopolymer such as a protein. However, this Kokai is silent on the subject of use as an adsorption or separation agent for cells or viruses.

SUMMARY OF THE INVENTION

One object of the present invention is to provide an improved separating agent which can be particularly utilized in a cell or virus separation process, and which, when used in a separation process, can simplify the separation pretreatment, preliminary operation, or operation per se, can conduct a rapid separation at low cost and with good reproducibility, and can ensure a remarkably increased separation capability.

Another object of the present invention is to provide an improved separating agent based on a calcium phosphate, which can be particularly utilized in the cell or virus separation process, and which has a higher adsorption and separation efficiency and satisfactory water retention, and possesses excellent stability.

Another object of the present invention is to provide an improved separating agent which, when used in the cell or virus separation process, can simplify the separation pretreatment, preliminary operation, or operation per se, can carry out the separation rapidly and at a low cost, can ensure a very good separation efficiency and performance, and can easily control the resulting separation pattern.

Still another object of the present invention is to provide an improved separator for separating a target cell or virus utilizing the above-described separating agents of the present invention, which enables one to conduct the cell or virus separation with high reproducibility and other advantages.

Still another object of the present invention is to provide an improved method of separating a cell or virus, in which the separating agents or separators of the present invention are utilized to conduct the separation satisfactorily.

These and other objects of the present invention will be more appreciated from the preferred embodiments of the present invention which will be described hereinafter.

In one aspect of the present invention, there is provided a separating agent for use with a cell or virus which consists of a polyvinyl acetal resin with a open cell structure having an average pore size of 10 to 1000 μm.

In another aspect of the present invention, there is provided a separating agent for use with a cell or virus which consists of porous calcium phosphate granules with an open cell structure, and in which the calcium phosphate granules have two distributions of pore size, wherein one has micropores ranging from 20 to 500 μm in average pore size and another one has small pores ranging from 1 to 50 μm in average pore size.

In still another aspect of the present invention, there is provided a separating agent for use with a cell or virus which consists of a polyvinyl acetal resin with an open cell structure having an average pore size of 10 to 1000 μm as a first element, and a layer of porous calcium phosphate granules having an average granule size of 50 to 2000 μm as a second element, applied onto the first element.

The above-described separating agent may further contain another polyvinyl acetal resin with an open cell structure having an average pore size of 10 to 1000 μm, as a third element applied over the second element to sandwich the second element between the first and third elements. The polyvinyl acetal resin forming the third element is preferably the same as the resin of the first element, but it may be different from the first element resin, if necessary and if it yields satisfactory results.

Further, in one aspect of the present invention, there is provided a separator for a cell or virus which comprises a container or column, filled with the above-described separating agents of the present invention.

Furthermore, in another aspect of the present invention, there is provided a method of separating a cell or virus which comprises passing a biological fluid containing the cell or virus to be separated through a column filled with the above-described separating agents of the present invention.

DESCRIPTION OF THE PREFERRED EMBODIMENTS

The first cell or virus separating agent according to the present invention is characterized by consisting of a polyvinyl acetal resin with an open cell structure having an average pore size (diameter) of about 10 to 1000 μm.

The separating agent of the present invention, as described above, is made from polyvinyl acetal resin having the desired pore size distribution. Polyvinyl acetal resins useful in the formation of the separating agent are those prepared by partially or completely acetalizing hydroxyl groups of polyvinyl alcohol with an aldehyde. The acetalization is represented by the following reaction schema:

in which
R is an alkyl group such as methyl, ethyl and butyl, and n is a positive integer.

Typical examples of the polyvinyl acetal resin used in the present invention include polyvinyl formal resin, polyvinyl butyral resin, and the like. These polyvinyl acetal resins can be prepared in accordance with any conventional manner well-known in the plastics industry. For example, they may be obtained by simultaneously hydrolyzing and acetalizing polyvinyl acetate, or by hydrolyzing polyvinyl acetate and then acetalizing the resulting polyvinyl alcohol. In any case, the hydrolysis should be substantially completed, and the acetalization should be carried out so that at least 50% of the hydroxyl groups in the polyvinyl alcohol are acetalized to produce the corresponding polyvinyl acetal resin having an acetalization rate of 50 to 100%. An acetalization rate of less than 50% should be avoided, since it causes deformation of the separating agent and reduction of the adsorption property thereof and thus of the separation performance, when a culturing solution or the like is applied to the element. Preferably, polyvinyl acetate used as a starting material in the production of the polyvinyl acetal resin has a polymerization degree of about 200 to 2000.

The polyvinyl acetal resin used in the present invention has open cells and an average pore size in the range of about 10 to 1000 $\mu$m. A pore size of less than 10 $\mu$m tends to cause a poor flow of the solution through the column and a clogging of the column, since it is too small in comparison with the size of the target cells. Further, a pore size of more than 1000 $\mu$m tends to cause a reduction of the separation performance due to a reduced surface area of the adsorption. The open cell structure of the polyvinyl acetal resin will be formed if the polymenzation is carried out in the presence of a foaming agent or in accordance with other well-known methods.

In addition to being formed from the polyvinyl acetal resin described in the above paragraphs, the cell or virus separating agent of the present invention preferably has a porous sponge structure, and more preferably is in the form of a spongy sheet. The sheet-like separating agent is preferably packed in the column of the separator, after it is fabricated into a disc having a diameter corresponding to the inner diameter of the column by using any fabrication method such as punching or cutting. Sufficient numbers of the disc to obtain a desired thickness of the separating agent or filler are layered or laminated in the column. If a granular or powdered resin is used, it is contemplated to simultaneously use a barrier means such as a strainer or filter to prevent the filled resin from flowing from the column. Note, spherical resin can easily clog during a cell or virus separation and can not maintain a uniform flow rate of the solution, because it is difficult to always maintain a uniform pore size of the resin. Accordingly, the use of spherical resin causes problems with reproducibility.

The separator for the cell or virus according to the present invention is characterized by comprising a container filled with a polyvinyl acetal resin with an open cell structure having an average pore size of about 10 to 1000 $\mu$m. The polyvinyl acetal resin used in the container was described hereinbefore with reference to the first separating agent.

The container used in the separator of the present invention may have any form which is conventional in the field of the cell or virus separation. For example, it may be a column, tube, pipe, syringe or the like. The polyvinyl acetal resin, as described above, is preferably filled in the container after its fabrication into disc form. The thickness of the layer of the filled resin in the container may vary depending upon various factors such as the specific cell or virus to be separated, the specific resin and the like.

Figure 1:
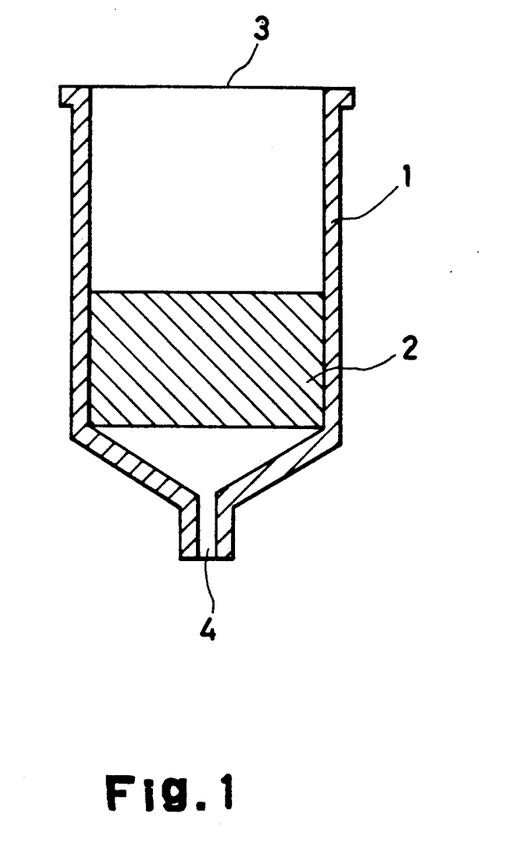
FIG. 1 is a cross-sectional view of the cell or virus separator according to a preferred embodiment of the present invention.

A typical example of a cell or virus separator according to the present invention is illustrated in FIG. 1, but the present invention should not be restricted to this example of the separator.

In the separator, a container or cylindrical column 1 contains the cell or virus separating agent 2 according to the present invention. Although not illustrated, the separating agent 2 is layer or a laminate of the sheet-like polyvinyl acetal resins. Of course, the separating agent 2 may be a layer of the polyvinyl acetal granules and in such a case, a strainer or filter means is preferably disposed in a bottom portion of the agent 2.

Using the separator of FIG. 1, a biological fluid containing the cell or virus to be separated is loaded through an inlet 3 onto the column 1. The separation is made while the biological fluid is passing through the separating agent 2, and only the non-adsorptive cells or viruses will be discharged through an outlet 4 of the separator.

The method of separating the cell or virus according to the present invention is characterized by comprising the step of passing a biological fluid through a container of the separator or column in which the above-described first separating agent is charged as a filler.

In the practice of the present invention, prior to the separation step, the column is generally pretreated with a washing solution to wash off undesirable contaminants and the like from the column. After the washing, the biological fluid is poured into the column. The biological fluid used herein is not restricted, and typical examples thereof include blood, serum, urine, saliva and a suspension of the cell and/or virus, as well as a diluted solution of whole blood wherein the blood is admixed with a suitable blood coagulation inhibitor and the mixture is diluted with a culturing solution to increase the volume of the mixture by one to ten times. Preferably, the cell suspension is used herein as the biological fluid. After the biological fluid has sufficiently infiltrated into the separating agent, washing is carried out with a washing solution to wash off and recover the nonadsorptive cells and the like from the column.

The washing solution and, if used, the suspending solution include, for example, a culturing medium such as Hank's ballance salt solution (HBSS), serum medium (RPMI-1640 et al.), or chemically defined medium, a physiological saline, or other solutions conventionally used as the washing solution in the field of this technology. The separation step is preferably carried out at a temperature of from room temperature to about 37° C. to avoid undesirable influences on or lesions of the cell or virus in the biological fluid.

Surprisingly and unexpectedly, the separated cell or virus has characteristics such as survival percentage or other properties which are substantially the same as those of the target cell or virus in the biological fluid. For example, T cells separated from the lymphocytes show an antibody production controllability and other characteristics which are substantially identical with those determined from the lymphocyte before the separation step.

In summary, according to the present invention discussed above, since the separating agent consists of polyvinyl acetal resin with an open cell structure and a pore size of about 10 to 1000 $\mu$m, the target cell or virus can be very stably separated from the biological fluid at a high separation performance, without altering the distribution of the cell or virus before and after separation, in comparison with the prior art separation process. Further, since complicated operations such as incubation are not required in the separation process, it is possible to notably simplify the separation operation and to significantly shorten the time required to accomplish the separation. Moreover, a one-step method can be used in the separation process, and the biological fluid containing the target cell or virus can be directly poured into the separating agent-filled column.

Further, the polyvinyl acetal resin used in the present invention can be commercially obtained at a low price and, if fabricated into the sheet-like separating agent, can be easily fitted in the column, after cutting of the sheet in conformity with the size and configuration of the column. The cutting of the sheet-like separating agent and fitting thereof can be rapidly made; in addition, one can omit any supporting means, which is generally used if a powder-like separating agent is charged in the column. Moreover, if the separator, i.e., separating agent filled column, is sterilized with any sterilization method such as sterilization with an ethylene oxide (EO) gas, the sterilized and sealed products can be easily put on the market.

Furthermore, since the separating agent is uniformly filled in the column and no clogging of the column is caused during the separation operation, a uniform flow rate of the biological fluid and accordingly an effective and stable separation of the cell or virus can be accomplished from the start to the end of the separation process. And, when a large amount of cells must be treated in the separation process, by varying the cross-sectional area of the polyvinyl acetal resin layer, the pore size of the resin, the layer thickness or height of the resin filled in the column, or other factors, the flow rate of the biological fluid through the column can be freely controlled to obtain the best results.

The second cell or virus separating agent according to the present invention is characterized by consisting of porous calcium phosphate granules with an open cell structure, and in which the calcium phosphate granules have two distributions of pore size, wherein one has micropores ranging from 20 to 500 nm (0.02 to 0.5 $\mu$m) in average pore size, and the other one has small pores ranging from 1 to 50 $\mu$m in average pore size.

The separating agent of the present invention, as described above, comprises porous calcium phosphate granules with two open cell structures. The granules have micropores having a pore size of 20 to 500 nm. This is because in the adsorption of the virus onto the calcium phosphate granules as the adsorption and separation agent, it is necessary to make the granules porous to extend the permeation path of the biological fluid in the column, and the size of the virus can vary depending upon the specific type thereof, but generally in the range of about 20 to 300 nm. Thus, to ensure passage of the virus through the pores of the granules, the pore size of the granules should be 20 nm or more. The upper limit of the pore size of these granules is 500 nm, since a pore size of more than 500 nm (which is notably larger than the virus size) has no critical meaning except that the potential of the adsorption is reduced with the increase of the pore size.

The calcium phosphate granules have small pores having a pore size of 1 to 50 $\mu$m in addition to the micropores. This is because to give a satisfactory amount of water retention to the granules, the granules should have small open cells of 1 to 50 $\mu$m such that the biological fluid such as the suspension of the cell or virus, can relatively easily pass through the column.

In addition to these two distributions of the pore size, the calcium phosphate granules used in the present invention preferably have a porosity of 10 to 75%. The porosity is important, because it can significantly affect the resulting water retention of the column. A porosity of less than 10% does not provide the water retention necessary to adsorb the cell or virus, and a porosity of more than 75% can not maintain the strength of the granules themselves.

Further, it is preferred that the calcium phosphate granules used have an average granule size of 10 to 2000 $\mu$m. For the cell separation, the cells can pass through the interstice between the granules, if the granule size is 100 $\mu$m or more (however, as described hereinafter, the granule size should be 10 $\mu$m or more in view of the virus separation). A granule size of more than 2000 $\mu$m is not acceptable, because the cells are not adsorbed on the separating material due to an excessively increased interstice between the granules. Moreover, a particle size of 1 $\mu$m or more is enough to carry out virus separation, but for practical use, it is preferred to select a particle size of 10 $\mu$m or more.

Furthermore, it is preferred that the calcium phosphate granules used have a Ca (calcium)/P (phosphorus) ratio of 1.4 to 1.8. More preferably, the granules have a Ca/P ratio of 1.5 to 1.67 to obtain a more improved sinterability and strength of the granules.

A wide variety of calcium phosphates can be used. Typical examples of useful calcium phosphates include apatites such as hydroxyapatite or fluoroapatite, $\alpha$- or $\beta$-tricalcium phosphate, tetracalcium phosphate, or a mixture of these compounds.

The calcium phosphate granules each can be produced in accordance with conventional methods. Crystalline particles of calcium phosphate obtained in the well-known wet process can be used as a starting material in this production of the granules. For example, the particulate calcium phosphate is suspended in water to produce a slurry, and then the slurry is subjected to spray drying or other treatments to make secondary particles, or the slurry is admixed with any additives such as viscosity modifiers, particles, or fibers of a thermally dissipating organic compound and the mixture is subjected to, e.g., spray drying to make the secondary particles. These are resuspended to obtain a slurry, which is molded under wet conditions to produce a molded block. During the molding process, an organic compound such as polyvinyl alcohol, methylcellulose, cellulose, or acrylic resin (beads), capable of being dissipated and forming small pores of 1 to 50 $\mu$m in the next sintering process may be added to the slurry to obtain the calcium phosphate porous granules. Of course, the resulting pore size can be controlled by the sintering temperature or other conditions without the organic compound. After molding, the block is sintered at a temperature of 500° to 1300° C. A temperature of less than 500° C. is not enough to cause a thermal dissipation of the added organic compound and to sinter the block, and a higher temperature beyond 1300° C. can cause excess sintering, thereby forming an excessively dense sintered block, or a decomposition of the calcium phosphate itself.

The sintered body is then crushed and sieved to obtain the desired calcium phosphate granules with the described pore size range. The size of micropores of 20 to 500 nm will be controlled suitably by selecting a grain size of the crystalline particles used in the starting slurry for the production of the secondary particles, the viscosity of the slurry, or the specific additive to the slurry. And, as described above, small pores of 1 to 50 $\mu$m will be produced by adding a thermally dissipating organic compound to the slurry of the secondary particles, or by suitably selecting a molding method and/or an additive in the molding of the block from the secondary particles.

The calcium phosphate granules can be also obtained by granulating the secondary particles using a granulator, followed by sintering.

The porous calcium phosphate granules can contain at least one modifier partially adsorbed thereon, to modify the physicochemical properties or immunological properties of the granule surface, thereby skillfully matching an adsorption activity to the particular target cell or virus group. As a result of this change of the adsorption activity, the separation characteristic of the column can be effectively changed to thereby obtain a separation characteristic capable of giving a sharp effluent pattern, or the separation spectrum can be controlled to obtain the best results. In addition, since it is possible to change or modify the adsorption activity to match each of the subpopulations of the cell or virus, a specific subpopulation can be selectively separated. Typical examples of the modifier adsorbed onto the granule surface include polysaccharides originated from a living body such as hyaluronic acid, chondroitin sulfuric acid, chitin derivatives, fibronectin or osteonectin, mucopolysaccharides and proteins as well as derivatives thereof.

The separator for the cell or virus according to the present invention is characterized by comprising a container having, filled therein, porous calcium phosphate granules with an open cell structure having two distributions of the pore size wherein one has micropores ranging from 20 to 500 nm in average pore size and the other one has small pores ranging from 1 to 50 μm in average pore size. The detailed descriptions of this separator will be omitted to avoid duplication, because the porous calcium phosphate granules used as a filler in the container were described hereinbefore with reference to the second separating agent and the container was described with reference to the cell or virus separator using the first separating agent.

A typical example of the separator using the second separating agent is not illustrated herein, but it is substantially the same as that of FIG. 1 except that the separating agent 2, i.e., the layer or laminate of the sheet-like polyvinyl acetal resins, is replaced with the described second separating agent or layer of the porous calcium phosphate granules, and the granule layer is preferably supported with a strainer or filter, for example, glass wool, in the column 1. Moreover, the operation and mechanism of the cell or virus separation in the separator are also substantially the same as those of the separator of FIG. 1 previously described.

The method of separating the cell or virus according to the present invention is characterized by comprising the step of passing a biological fluid through a column in which the above-described second separating agent is charged as a filler.

The separation of the cell or virus from the biological fluid by using the second separating agent described above can be similarly carried out as in the separation described hereinbefore, in detail, with regard to the cell or virus separation using the first separating agent. Namely, any biological fluid containing the target cell or virus can be subjected to the separation process of the present invention, and the biological fluids which maybe used include, for example, blood, serum, urine, saliva, and a suspension of the cell and/or virus.

The separation process of the present invention can be used to advantage for many purposes, such as removal of virus from the biological fluid, recovery of specific cell groups such as recovery of T cells from the whole blood or lymphocytes, and other purposes. Particularly, in the separation of cells from whole blood, it is preferred that after letting blood from a human body, the blood is admixed with a blood coagulation inhibitor such as heparin or citric acid, and the mixture is diluted with a culturing solution as a diluent to increase the volume of the mixture by one through ten times. As a result of the dilution of the blood, separation of the cells is accelerated, because the viscosity of the blood is reduced. However, dilution of the blood beyond ten times should be avoided, since it causes an unacceptable increase in the amount of the mixture to be treated.

Practically, the separation process of the present invention can be preferably carried out in accordance with the following manner. To ensure retention of the separating agent in a container such as column in the separator, a filling material such as glass wool is filled in an outlet portion of the container. Next, the separating agent or porous calcium phosphate granules are filled in a central portion of the container. The filled separating agent can be washed with any suitable washing solution to remove contaminants and the like. After the completion of washing, a biological fluid containing the target cell or virus is poured in the container. After the biological fluid has sufficiently permeated through the separating agent of the container, the separating agent is again washed with the washing solution to remove and recover the nonadsorptive cell or virus.

The suspending or washing solution used in the separation process of the present invention can be suitably selected from the well-known solutions depending upon the specific cell or virus to be separated. Typical examples of these solutions and the preferred range of the temperature in the separation process were described hereinbefore.

As is apparent from the above descriptions and as is demonstrated in the attached working examples, the adsorption/separation agent of the present invention can exhibit a high adsorption performance with regard to the virus and animal or plant cells and therefore can be effectively utilized to separate these viruses and cells from biological fluid.

Particularly, the separating agent of the present invention is suitable to separate T cells from a biological fluid such as whole blood, since it has no influence on the T cells, while the B cells and macrophages can be selectively adsorbed on the separating agent. More particularly, since the T cells can be recovered at a high purity without changing the distribution of the subsets thereof, the separating agent can be advantageously utilized in immunological studies and clinical tests, in addition to the analysis of the T cells. As examples of the clinical tests in which the present separating agent can be utilized, there are mentioned tests such as determination of the distribution of the T cells and function tests. These tests are adopted in the treatment of cancer, autoimmune disease, AIDS and other diseases. For clinical testing wherein after blood-letting, the whole blood itself is immediately examined in a test apparatus, it is contemplated to previously remove the B cells and macrophages from the whole blood, thereby enabling a high accuracy examination of the T cells.

In addition to these advantages, according to the present invention, it is possible to carry out the cell or virus separation with high reproducibility and a shortened separation time, because the separation agent of the present invention has a sufficiently improved water retention and also an excellent micropore structure. Further, in a separation using the separation of the present invention, since an incubation step is not required, it is also possible to notably simplify the separation operation.

The third cell or virus separating agent according to the present invention is characterized by consisting of a polyvinyl acetal resin with an open cell structure having an average pore size of 10 to 1000 μm as a first element, and a layer of porous calcium phosphate granules having an average granule size of 10 to 2000 μm as a second element, applied onto the first element. The first element and the second element used herein correspond to the first separating agent and the second separating agent, described hereinbefore, respectively. Namely, the present invention is based on the finding that notably excellent effects can be also obtained if the first separating agent is used in combination with the second separating agent in a container of the cell or virus separator.

The porous calcium phosphate granules used as the second element may have two distributions of pore size wherein one distribution has micropores ranging from 20 to 500 nm (0.02 to 0.5 μm) in average pore size and the other one has small pores ranging from 1 to 50 μm in average pore size. In the porous calcium phosphate granules, the lower limit of the pore size is 20 nm (0.02 μm), because, as described hereinbefore, the virus generally has a size of about 20 to 300 nm.

In a preferred embodiment of the present invention, the third separating agent may further contain another polyvinyl acetal resin with an open cell structure having an average pore size of 10 to 1000 μm, as a third element, applied over the second element to sandwich the second element between the first and third elements. The polyvinyl acetal resin of the first element and that of the third element may be substantially the same or different, as previously mentioned.

The polyvinyl acetal resin used as the first and third elements of the third separating agent according to the present invention may be substantially the same as the polyvinyl acetal resin as the first separating agent which has already been explained in detail, and therefore the detailed description of this polyvinyl acetal resin is omitted herein to avoid duplication of the description. However, it should be noted that in the third separating agent the polyvinyl acetal resin as the first element can play two roles, namely, (1) as a cell or virus separating agent and (2) as a filter means which can prevent the calcium phosphate granules disposed thereon from flowing out. Accordingly, the polyvinyl acetal resin is preferably used in the form of a spongy sheet.

Similarly, the porous calcium phosphate granules used as the second element of the third separating agent may be substantially the same as the porous calcium phosphate granules of the second separating agent which has already been explained in detail. For the details of these porous calcium phosphate granules, refer to the previous descriptions concerning the second separating agent.

The separator for the cell or virus according to the present invention is characterized by comprising a container having, filled therein, a polyvinyl acetal resin with an open cell structure having an average pore size of 10 to 1000 μm as a first element, and a layer of porous calcium phosphate granules having an average granule size of 10 to 2000 μm as a second element, applied onto the first element. Moreover, the separator of the present invention is characterized by using the above-described third separating agent as a filler in a container of the separator, and the container may be of the same types as those described hereinbefore.

Figure 2:
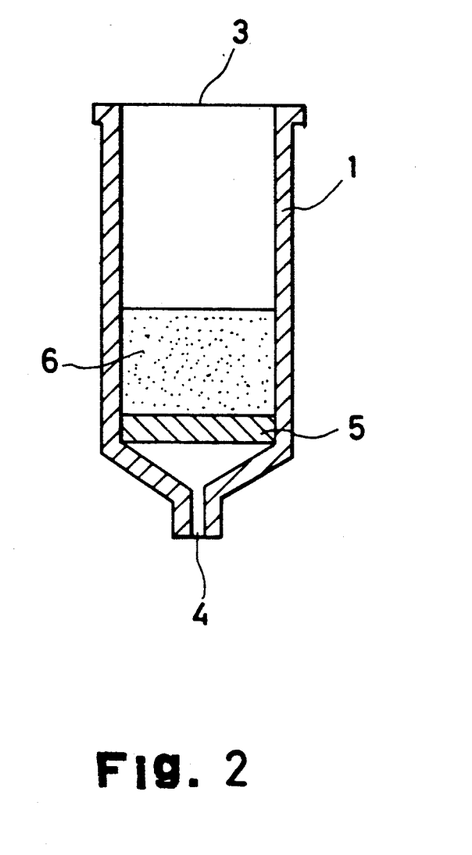
FIG. 2 is a cross-sectional view of the cell or virus separator according to another preferred embodiment of the present invention.
Figure 3:
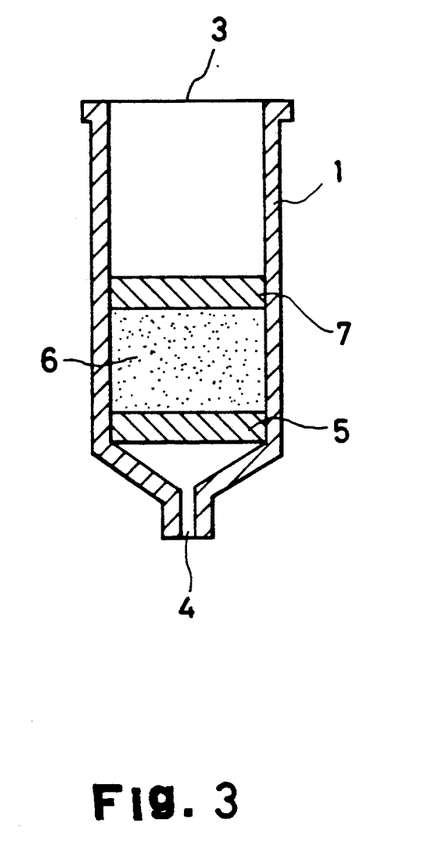
FIG. 3 is a cross-sectional view of the cell or virus separator according to another preferred embodiment of the present invention.

Two typical examples of the cell or virus separator according to the present invention are illustrated in FIGS. 2 and 3.

In the separator of FIG. 2, a container or column 1 contains the third separating agent of the present invention which, as illustrated, consists of a porous sheet 5 of the polyvinyl acetal resin and a layer 6 of the porous calcium phosphate granules. Using this separator, a biological fluid containing the target cell or virus is poured through an inlet 3 into the column 1. The separation of the target cell or virus is made during passage of the biological fluid through, in sequence, the porous granule layer 6 and porous sheet 5. The treated biological fluid is eluted through an outlet 4 of the separator. Note, the separator of FIG. 3 is substantially the same as this separator of FIG. 2, with the proviso that as illustrated in FIG. 3, a sandwich structure consisting of a porous sheet 5 of the polyvinyl acetal resin, a layer 6 of the porous calcium phosphate granules and another porous sheet 7 of the polyvinyl acetal resin was used as the third separating agent.

The method of separating the cell or virus according to the present invention is characterized by comprising the step of passing a biological fluid through a column in which the above-described third separating agent is charged as a filler. This separation method can be similarly carried out, with similar good results, as in the separation methods described hereinbefore with regard to the cell or virus separations using the first and second separating agent, and therefore a detailed description of this method would be essentially redundant.

As is apparent from the above descriptions and as is demonstrated in the attached working examples, excellent synergistic effects can be obtained in the practice of the present invention, since the first separating agent is used in combination with the second separating agent in a column of the separator. For example, in contrast to the prior art separator, the separator of the present invention has a very stable and high separation performance, and also can separate the target cells or virus from the biological fluid without changing the distribution of the cells or virus. Further, using the separator of the present invention, the biological fluid can be poured directly on the separating column in a single step, since complex operations such as incubation are not required in the separation process. This means that the separation operation can be significantly simplified, and the required separation time can be substantially shortened.

The present invention will now be further described with reference to working examples which, however, do not restrict the scope of the present invention. The separators illustrated in FIGS. 1 to 3 were used to carry out these examples.

EXAMPLE 1

A syringe-type column having an internal volume of 5 ml was filled with small cut sheets of the polyvinyl formal resin ("SPONGE BELL-ETA", product of Kanebo) having an average pore size of 100 μm and a formalization rate of 80 to 86% to produce a cell separator with a volume of 2 ml. The small cut sheet had a 13 mm diameter and 16 mm of thickness. The filler of the column was washed, in sequence, with distilled water and HBSS maintained at 37° C. After washing, 0.2 ml of the HBSS containing mononuclear cells suspended therein was loaded onto and permeated into the filler. The mononuclear cells were those previously isolated from normal human peripheral blood in accordance with a conventional density gradient centrifugation. After the permeation was completed, the nonadsorptive cells were removed from the column by again washing the filler with the HBSS.

In this cell separation, the following three tests were carried out to evaluate the separation performance of the separator used.

Test 1

The number of cells was counted with a hemocytometer both before and after the passage of the cell suspension through the column. The results of this test are summarized in Table 1.

Test 2

The state of the cell separation was examined. To conduct this examination, the cells in the effluent from the column were stained with fluorescein-conjugated antibodies, CD3(anti-Leu 4) or CD19(anti-Leu 12), and then the percentage of the T cells and B cells was determined using a fluorescence activated cell sorter (FACS). The results of this test are summarized in Table 2.

Test 3

Distribution of T cell subsets was determined. To conduct this determination, the cells in the effluent from the column were stained with the fluorescein-conjugated antibodies, CD8(anti-Leu 2a) or CD4(anti-Leu 3a), and then the percentage of the suppressor and helper T cells was determined using the FACS. The results of this test are summarized in Table 3. Time required in separation:

The time required from the preparation of the column to the completion of the separation was recorded. The result is summarized in Table 4.

EXAMPLE 2

The procedure of Example 1 was repeated except that small cut sheets of the polyvinyl formal resin having an average pore size of 500 μm and a formalization degree of 80 to 86% were used.

The results of the Tests 1, 2 and 3 and time required in the separation are summarized in Tables 1 to 4, respectively.

EXAMPLE 3

The procedure of Example 1 was repeated except that small cut sheets of the polyvinyl butyral resin having an average pore size of 100 μm and a butyralization degree of 80 to 86% were used.

The results of Tests 1, 2 and 3 and the time required in the separation are summarized in Tables 1 to 4, respectively.

COMPARATIVE EXAMPLE 1

A commercially available nylon wool was dipped in a voluminous 0.1N solution of HCl overnight. The wool was then washed several times in deionized water, with flexing. The washed wool was then dried at 30° C. for 3 hours. In this manner, the pretreated nylon wool was obtained.

A syringe-type column having an internal volume of 5 ml, as used in Example 1, was filled with 0.25 g of the pretreated nylon wool to produce a cell separator with a volume of about 3 ml. The filler of the column was washed, in sequence, with physiological saline and Hank's medium maintained at 37° C. After washing, 0.2 ml of monocyte suspension in HBSS with floating monocytes was poured on and permeated into the filler. The monocytes were those previously isolated from normal human peripheral blood in accordance with a conventional specific gravity centrifugation method. After permeation of the HBSS, incubation was continued at 37° C. for 1 hour. The nonadsorptive cells were then removed from the column by again washing the filler with Hank's medium.

In this cell separation, Tests 1, 2 and 3 of Example 1 were carried out in accordance with the manner described in Example 1, to evaluate the separation of the separator used. The results of these test are summarized together with the time required in the separation, in Tables 1 to 4.

TABLE 1

| Recovery of Cells | |
|---|---|
| Example No. | Recovery (%) |
| Example 1 | 57 |
| Example 2 | 50 |
| Example 3 | 49 |
| Comparative Example 1 | 25 |

TABLE 2

| | State of Cell Separation (percentage: %) | |
|---|---|---|
| Example No. | T cells (CD3) | B cells (CD19) |
| Example 1 | 84.3 | 0.8 |
| Example 2 | 85.3 | 0.9 |
| Example 3 | 84.7 | 0.8 |
| Comparative Example 1 | 82.6 | 2.0 |
| Control* | 79.8 | 7.6 |

*Control... determined before passing through column

TABLE 3

| | Distribution of T Cell Subsets (percentage: %) | |
|---|---|---|
| Example No. | Suppressor (CD8) | Helper (CD4) |
| Example 1 | 34.0 | 44.6 |
| Example 2 | 35.2 | 43.7 |
| Example 3 | 37.1 | 42.6 |
| Comparative Example 1 | 58.2 | 29.5 |
| Control* | 30.4 | 50.1 |

*Control... determined before passing through column

TABLE 4

| Time Required in Separation | |
|---|---|
| Example No. | Time Requirement |
| Example 1 | 30 min. |
| Example 2 | 30 min. |
| Example 3 | 30 min. |
| Comparative Example 1 | 2 days |

As is apparent from these results, according to the present invention, excellent recovery and separation performances which are notably higher than those of the prior art filler (nylon wool) can be stably obtained. Also, the distribution of the separated T cell subsets is substantially the same before and after separation. Moreover, according to the present invention it is possible to achieve rapid separation, because the long washing and 1 hour incubation essential to the prior art may be omitted. While in Examples 1 to 3 the present invention was described with regard to the separation and recovery of T cells, similar results can be obtained in the separation of other cells or viruses.

EXAMPLE 4

Calcium phosphate (Ca/P ratio=1.67) was synthesized by conventional wet method and then granulated by spray-dryer to obtain calcium phosphate powder. The powder was mixed with distilled water and the mixture was molded according to the conventional wet molding method, and then dried. Calcium phosphate granules were obtained by crushing the dried body. After sieving, the granules were sintered at 1200° C. to produce porous hydroxyapatite granules having a porosity of 20% and a granule size of 300 to 600 μm. In these granules, micropores had an average pore size of 20 nm, and small pores an average pore size of 2 μm, respectively.

A syringe-type column having an internal volume of 6 ml was filled with 0.03 g of glass wool up to the 1 ml mark. Next, the column was filled with 1 g of the porous hydroxyapatite granules to produce a virus separator.

A suspension of PR8 influenza virus in a physiological saline solution was loaded on the column of the separator, and a titer of the virus suspension passed through the column was determined in accordance with the titer determination method described below. Results of the determination are summarized in Table 5.

Determination of Titer

Chicken red blood cells are aggregated with each other. When influenza virus is adhered to the red blood cells. Based on this aggregation reaction, a titer is determined. Namely, a virus suspension is diluted with a physiological saline solution (0.9% aqueous solution of sodium chloride) to make a twice-diluted suspension, i.e., 2× suspension, 4× suspension, 8× suspension, 16× suspension, etc. These diluted suspensions are mixed with the same amount of a 0.4% suspension of chicken red blood cells to determine the degree of dilution at which the aggregation reaction is caused. The titer of the stock suspension (undiluted suspension) is evaluated from the determined degree of dilution.

EXAMPLE 5

The procedure of Example 4 was repeated except that the hydroxyapatite granules had a granule size of 100 to 300 μm. Results of the titer determination are summarized in Table 5.

EXAMPLE 6

The procedure of Example 4 was repeated except that the hydroxyapatite granules had a granule size of 100 to 300 μm and the column was filled with 3 g of the granules. Results of the titer determination are summarized in Table 5.

EXAMPLE 7

Hydroxyapatite (Ca/P ratio=1.67) granules obtained by the process described in Example 4 were sintered at 900° C. to produce porous hydroxyapatite granules having a porosity of 45% and a granule size of 100 to 300 μm. In these granules, the micropores had an average pore size of 50 nm, and the small pores an average pore size of 4 μm, respectively.

Using 1 g of the resulting granules, virus separation was carried out in accordance with the manner described in Example 4, and a titer of the virus suspension passed through the column was determined in accordance with the method described in Example 4. Results of the determination are summarized in Table 5.

EXAMPLE 8

Hydroxyapatite (Ca/P ratio=1.67) granules obtained by the process described in Example 4 were sintered at 700° C. to produce porous hydroxyapatite granules having a porosity of 60% and a granule size of 100 to 300 μm. In these granules, the micropores had an average pore size of 100 nm, and the small pores an average pore size of 6 μm, respectively.

Using 1 g of the resulting granules, a virus separation was made in accordance with the manner described in Example 4, and the titer of the virus suspension passed through the column was determined in accordance with the method described in Example 4. Results of the determination are summarized in Table 5.

EXAMPLE 9

The procedure of Example 8 was repeated except that the column was filled with 2 g of the granules. Results of the titer determination are summarized in Table 5.

EXAMPLE 10

Calcium phosphate (Ca/P ratio=1.5) granules obtained by the process described in Example 4 were sintered at 1100° C. to produce porous calcium phosphate granules having a porosity of 30% and a granule size of 100 to 300 micrometers. The micropores of these granules had an average pore size of 300 nm, and the small pore had an average pore size of 8 micrometers, respectively. Using 1 g of the resulting granules, the virus separation was made in accordance with Example 4, and a titre of the virus suspension passed through the column was likewise determined as in Example 4. Results of the determination are summarized in Table 5.

EXAMPLE 11

Calcium phosphate (Ca/P ratio=1.5) granules obtained by the process described in Example 4 were sintered at 700° C. to produce porous calcium phosphate granules having a porosity of 60% and a granule size of 100 to 300 μm. In these granules, the micropores had an average pore size of 100 nm, and the small pores an average pore size of 10 μm, respectively.

Using 1 g of resulting granules, the virus separation was carried out in accordance with the manner described in Example 4, and a titer of the virus suspension passed through the column was determined in accordance with the method described in Example 4. Results of the determination are summarized in Table 5.

EXAMPLE 12

The procedure of Example 11 was repeated except that the column was filled with 2 g of the granules. Results of the titer determination are summarized in Table 5.

EXAMPLE 13

Calcium phosphate (Ca/P ratio=1.57) granules obtained by the process described in Example 4 were sintered at 1100° C. to produce porous calcium phosphate granules having a porosity of 25% and a granule size of 100 to 300 micrometers. The micropores of these granules had an average pore size of 50 nm; the small pores had an average pore size of 3 micrometers. Using 1 g of the resulting granules, the virus separation was carried out in accordance with Example 4, and a titre of the virus suspension passed through the column was determined as in Example 4. Results are shown in Table 5.

COMPARATIVE EXAMPLE 2

Calcium phosphate (Ca/P ratio=1.67) powder was obtained as described in Example 4. The powder was molded by conventional dry pressing to obtain a green compact. Calcium phosphate granules were obtained by crushing this green compact. After sieving, the granules were sintered at 700° C. to produce porous calcium phosphate granules containing only micropores having an average pore size of 50 nm and having a porosity of 50% and a granule size of 100 to 300 $\mu$m. Results of the titer determination are summarized in Table 5.

COMPARATIVE EXAMPLE 3

The procedure of Comparative Example 2 was repeated except that the column was filled with 2 g of the granules. Results of the titer determination are summarized in Table 5.

TABLE 5

| Example No. | Titer |
|---|---|
| Control* | 128 |
| Example 4 | 32 |
| Example 5 | 8 |
| Example 6 | 8 |
| Example 7 | 8 |
| Example 8 | 4 |
| Example 9 | 0 |
| Example 10 | 8 |
| Example 11 | 4 |
| Example 12 | 0 |
| Example 13 | 4 |
| Comparative Example 2 | 64 |
| Comparative Example 3 | 64 |

*Control ... determined before passing through column

From the results of Table 5, it is appreciated that the titer is in proportion to the concentration of the influenza virus in the effluent per unit volume. Accordingly, while Example 4 showed the worst titer among Examples 4 to 13, the titer obtained is about half of the titer of Comparative Examples Nos. 2 and 3. Further, Examples 9 and 12 show that all of the virus was substantially completely adsorbed on the adsorption agent. This means that the porous calcium phosphate granules have an excellent adsorption performance. Furthermore, as is appreciated from the results of the Examples 8, 9, 11 and 12, the granules of the present invention can increase the amount of the virus to be adsorbed thereon, with increase of the filling amount thereof. In contrast, Comparative Example No. 3 shows that although twice the amount of the granules of Comparative Example No. 2 was used, no increase in the adsorbed amount could be obtained.

EXAMPLE 14

A syringe-type column having an internal volume of 6 ml was filled with 0.03 g of glass wool up to the 1 ml mark. Further, the column was filled with 1 g of the porous hydroxyapatite granules of Example 4 to produce a cell separator.

Thereafter, a suspension of $5 \times 10^6$ lymphocytes in a volume of 0.2 ml HBSS was loaded onto and permeated into the filler of the cell separator. The lymphocytes were obtained from normal human peripheral blood. After the suspension was sufficiently permeated into the granules of the filler, the filler was washed with 3 ml of HBSS to remove the nonadsorptive cells from the filler. The removed and recovered cells were stained with fluorescein-conjugated antibodies, CD3(anti-Leu 4) or CD19(anti-Leu 12), and then the percentage of T cells and B cells was determined using the FACS in accordance with the manner described in Example 1. The results of this test are summarized in Table 6.

EXAMPLE 15

The procedure of Example 14 was repeated except that porous hydroxyapatite granules having a porosity of 45% and a granule size of 300 to 600 $\mu$m were used as a filling material. The granules were produced by sintering hydroxyapatite (Ca/P ratio=1.67) at 900° C. In these granules, the micropores had an average pore size of 50 nm, and the small pores an average pore size of 4 $\mu$m, respectively. The results of the determination of the positive percentage are summarized in Table 6.

EXAMPLE 16

The procedure of Example 14 was repeated that porous hydroxyapatite granules having a porosity of 60% and a granule size of 300 to 600 $\mu$m were used as a filling material. The granules were produced by sintering hydroxyapatite (Ca/P ratio=1.67) at 700° C. In these granules, the micropores had an average pore size of 100 nm, and the small pores an average pore size of 6 $\mu$m, respectively. The results of the determination of the positive percentage are summarized in Table 6.

COMPARATIVE EXAMPLE 4

The procedure of Example 14 was repeated that porous hydroxyapatite granules, which were obtained according to the process described in Comparative Example 2, having a porosity of 50% and a granule size of 300 to 600 $\mu$m were used as a filling material. The granules were produced by sintering hydroxyapatite (Ca/P ratio=1.67) at 700° C. The resulting granules contained only micropores having an average pore size of 50 nm. The results of the determination of the positive percentage are summarized in Table 6.

TABLE 6

| | State of Cell Separation (percentage: %) | |
|---|---|---|
| Example No. | T cells (CD3) | B cells (CD19) |
| Control* | 90.9 | 7.4 |
| Example 14 | 96.2 | 2.1 |
| Example 15 | 96.7 | 1.9 |
| Example 16 | 97.5 | 1.3 |
| Comparative Example 4 | 94.0 | 4.2 |

*Control ... determined before passing through column

In the Examples 14, 15 and 16, it is considered that a gradual increase (of the amount of the adsorbed B cells)

was caused because of the corresponding gradual increase of the volume of the granules used. Note, in spite of the lower volume of the granules, Examples 14 and 15 resulted in better adsorption performance in comparison with Comparative Example 4, and also Example 14 showed a higher adsorption than Comparative Example 4.

EXAMPLE 17

Hydroxyapatite (Ca/P ratio=1.67) granules obtained by the process described in Example 4 were sintered at 1200° C. to produce porous hydroxyapatite granules having a porosity of 20% and a granule size of 300 to 600 μm. In these granules, the micropores had an average pore size of 20 nm, and the small pores an average pore size of 2 μm, respectively.

A syringe-type column having an internal volume of 6 ml was filled with, in sequence, 0.03 g of the glass wool up to the 1 ml mark and 1 g of the porous hydroxyapatite granules produced in the previous step to make a column separator.

Thereafter, 1 ml of blood was loaded onto the column and the blood eluted from the column was recovered. The blood tested contained 13% of citric acid added as a blood coagulation inhibitor. The cells in the recovered blood were stained with fluorescein-conjugated antibodies, CD3 (anti-Leu 4) or CD19 (anti-Leu 12), the red blood cells were hemolyzed with $NH_4Cl$, and the percentage of the T cells and B cells was determined in the FACS in accordance with the manner described in Example 1. The results of this test are summarized in Table 7.

EXAMPLE 18

The procedure of Example 17 was repeated except that the blood tested did not contain citric acid, but after sampling, the blood was diluted with HBSS to double the volume, and 2 ml of the diluted blood was poured on the column. The results of the determination of the positive percentage are summarized in Table 7.

EXAMPLE 19

The procedure of Example 17 was repeated except that the blood tested did not contain citric acid, but after sampling, the blood was diluted with HBSS to four times the starting volume, and 4 ml of the diluted blood was poured on the column. The results of the determination of the positive percentage are summarized in Table 7.

TABLE 7

| Example No. | State of Cell Separation (percentage: %) | |
|---|---|---|
| | T cells (CD3) | B cells (CD19) |
| Control* | 90.1 | 8.8 |
| Example 17 | 95.2 | 4.0 |
| Example 18 | 96.7 | 2.9 |
| Example 19 | 96.5 | 2.7 |

*Control ... determined before passing through column

Examples 4 to 19 were particularly described with reference to the separation of influenza virus or lymphocyte cells, but the cell or virus separating agents of the present invention can similarly apply to the separation of other virus and cells from biological fluid with satisfactory results. Moreover, the separating agent of the present invention can be utilized as an adsorbent for plant cells such as "sugi (ceder)" pollen which is the cause of pollinosis.

EXAMPLE 20

A syringe-type column having an internal volume of 5 ml was filled with a small cut sheet of polyvinyl formal resin ("SPONGE BELL-ETA" product of Kanebo) having an average pore size of 100 μm and a formalization rate of 80 to 86% to make a volume of 0.2 ml. The small cut sheet was 13 mm in diameter and 2 mm thick. Next, the column was filled with 1 g of porous hydroxyapatite granules (Ca/P ratio=1.67), which were obtained by the process described in Example 4, having a granule size of 300 to 600 μm, sintered at 700° C. The column was finally filled with the same cut sheet of polyvinyl formal resin as described above to make a volume of 0.2 ml. A cell separator containing a filler of the sandwich structure was thus produced. The filler of the separator was washed with a HBSS maintained at 37° C. After washing, 0.2 ml of a suspension of mononuclear cells in HBSS was loaded onto and permeated into the filler. The mononuclear cells were those previously isolated from human peripheral blood in accordance with a conventional density gradient centrifugation. After the permeation was completed, the nonadsorptive cells were removed from the column by again washing the filler with the HBSS. Note, the pores of the hydroxyapatite granules used herein consisted of micropores having an average pore size of 0.1 μm and small pores having an average pore size of 6 μm.

In this cell separation, to evaluate the separation performance of the separator, Tests 1, 2 and 3 as described in Example 1 were carried out. The results of Tests 1, 2 and 3 as well as the time required from the preparation of the column to the completion of the separation are summarized in the following Tables 8 to 11, respectively.

EXAMPLE 21

The procedure of Example 20 was repeated except that the hydroxyapatite granules used herein are those sintered at 900° C. and the pores thereof consist of micropores having an average pore size of 0.05 μm and small pores having an average pore size of 4 μm.

The results of Tests 1, 2 and 3 and the time required in the separation are summarized in Tables 8 to 11, respectively.

EXAMPLE 22

The procedure of Example 20 was repeated except that the hydroxyapatite granules used herein are those sintered at 1200° C. and the pores thereof consist of micropores having an average pore size of 0.02 μm and small pores having an average pore size of 2 μm.

The results of the Tests 1, 2 and 3 and the time required in the separation are summarized in Tables 8 to 11, respectively.

EXAMPLE 23

The procedure of Example 20 was repeated except that small cut sheets of polyvinyl butyral resin (product of Sekisui Chemical) having an average pore size of 500 μm and a butyralization rate of 80 to 86% were used instead of the polyvinyl formal resin, and that the column was filled with 2 g of porous calcium phosphate granules (Ca/P ratio=1.67) having a granule size of 300 to 1200 micrometers, sintered at 1200° C. The granules have micropores (average pore size=0.05 micrometers), and small pores (average pore size=20 micrometers).

The results of Tests 1, 2 and 3 and the time required in the separation are summarized in Tables 8 to 11, respectively.

COMPARATIVE EXAMPLE 5

Finely divided nylon wool was dipped in a voluminous 0.1N HCl solution over one night, and then washed several times in deionized water, with flexing. The washed wool was then dried at 30° C. for 3 hours. The pretreated nylon wool was thus obtained.

A syringe-type column having an internal volume of 5 ml was filled with 0.25 g of the pretreated nylon wool up to the 3 ml mark to produce a cell separator. The filler of the column was washed, in sequence, with a physiological saline solution and HBSS maintained at 37° C. After washing, 0.2 ml of the suspension of monocytes in the HBSS was loaded onto and permeated into the nylon wool. The monocytes were those previously isolated from normal human peripheral blood in accordance with a conventional specific gravity centrifugation method. After permeation of the Hank's medium, an incubation was continued at 37° C. for one hour, and then the nonadsorptive cells were removed from the column by again washing the filler with the Hank's medium.

In this cell separation, Tests 1, 2 and 3 of Example 1 were carried out in accordance with the manner described in Example 1, to evaluate the separation of the separator used. The results of these tests are summarized together with the time required in the separation, in Tables 8 to 11.

TABLE 8

| Recovery of Cells | |
|---|---|
| Example No. | Recovery (%) |
| Example 20 | 92 |
| Example 21 | 95 |
| Example 22 | 89 |
| Example 23 | 88 |
| Comparative Example 5 | 24 |

TABLE 9

| | State of Cell Separation (percentage: %) | |
|---|---|---|
| Example No. | T cells (CD3) | B cells (CD19) |
| Example 20 | 80.3 | 0.4 |
| Example 21 | 80.2 | 2.0 |
| Example 22 | 80.3 | 1.5 |
| Example 23 | 80.5 | 2.1 |
| Comparative Example 5 | 79.8 | 3.5 |
| Control* | 78.0 | 5.7 |

*Control . . . determined before passing through column

TABLE 10

| | Distribution of T cell subsets (percentage: %) | |
|---|---|---|
| Example No. | Suppressor (CD8) | Helper (CD4) |
| Example 20 | 32.1 | 53.3 |
| Example 21 | 32.3 | 53.5 |
| Example 22 | 32.2 | 53.3 |
| Example 23 | 31.8 | 53.6 |
| Comparative Example 5 | 57.8 | 30.1 |

TABLE 10-continued

| | Distribution of T cell subsets (percentage: %) | |
|---|---|---|
| Example No. | Suppressor (CD8) | Helper (CD4) |
| Control* | 29.1 | 53.6 |

*Control . . . in blood

TABLE 11

| Time Required in Separation | |
|---|---|
| Example No. | Time Requirement |
| Example 20 | 45 min. |
| Example 21 | 45 min. |
| Example 22 | 45 min. |
| Example 23 | 40 min. |
| Comparative Example 5 | 2 days |

As is apparent from these results, according to the present invention, excellent recovery and separation performance which are notably higher than those of the prior art filler (nylon wool) can be stably obtained. Also, distribution of the separated T cell subsets is substantially the same before and after separation. Moreover, according to the present invention it becomes possible to conduct a rapid separation, because the long-time washing and one hour incubation which was essential to the nylon wool filler can be omitted.

EXAMPLE 24

A syringe-type column having an internal volume of 5 ml was filled with small cut sheets of polyvinyl formal resin ("SPONGE BELL-ETA" product of Kanebo) having an average pore size of 50 μm and a formalization degree of 80 to 86% to make a volume of 0.2 ml. The sheet was 13 mm in diameter and 2 mm thick. Next, the column was filled with 1 g of porous calcium phosphate granules (Ca/P ratio=1.67) obtained by the process of Example 4, having a granule size of 100 to 300 μm, sintered at 1200° C. The column was finally filled with the same cut sheet of the polyvinyl formal resin as described above to again make a volume of 0.2 ml. A virus separator containing a filler of the sandwich structure was thus produced. The calcium phosphate granules used herein have micropores having an average pore size of 0.02 micrometers, and small pores having an average pore size of 2 micrometers.

A suspension of PR8 influenza virus in a physiological saline solution was poured on the column of the separator, and a titer of the virus suspension passed through the column was determined in accordance with the titer determination method described in Example 4. Results of the determination are summarized in Table 12.

EXAMPLE 25

The procedure of Example 24 was repeated except that the calcium phosphate granules used were those sintered at 700° C., having a granule size of 100 to 200 micrometers, micropores with average pore size of 0.1 micrometers, small pores with average pore size of 6 micrometers, and a Ca/P ratio of 1.67. Results of the titre determination are shown in Table 12.

EXAMPLE 26

The procedure of Example 24 was repeated, except that the porous calcium phosphate granules and the calcium phosphate granules used herein were those sintered at 700° C., having a granule size of 100 to 300 micrometers, micropores with an average pore size of 0.1 micrometers, small pores with an average pore size of 10 micrometers, and a Ca/P ratio of 1.5. Results of the titre determination are shown in Table 12.

COMPARATIVE EXAMPLE 6

The procedure of Example 24 was repeated, except that the column was filled, in sequence, with 0.03 g (1 ml) of the glass wool and 1 g of calcium phosphate granules. These granules were obtained by the process described in Example 4 and sintered at 700° C., thus having a granule size of 100 to 200 μm, micropores with an average pore size of 0.1 μm, small pores with an average pore size of 6 μm and a Ca/P ratio of 1.67. Results of the titer determination are summarized in the following Table 12.

TABLE 12

| Example No. | Titer |
|---|---|
| Control* | 128 |
| Example 24 | 16 |
| Example 25 | 4 |
| Example 26 | 4 |
| Comparative Example 6 | 8 |

*Control ... determined before passing through column

The results of Table 12 indicate that according to the present invention, viruses can be effectively adsorbed and separated. Further, in a comparison of Example 25 with comparative Example 6, using the same amount of the filler, good results and accordingly good adsorption of the virus can be accomplished using the procedure of Example 25. Note, according to the present invention, satisfactory results can be similarly obtained in the separation of other viruses and/or cells than the above-described influenza virus and T cell.

We claim:

1. A separating agent for separating at least one of cells and viruses comprising:
   a first distribution and a second distribution of porous calcium phoshate granules having an open cell structure;
   said first distribution of porous calcium phosphate granules having a distribution of micropores ranging from 20 to 500 nm in average pore size; and
   said second distribution of porous calcium phosphate granules having a distribution of small pores ranging from 1 to 50 μm in average pore size.

2. The separating agent according to claim 1, wherein said calcium phosphate granules have a porosity of 10 to 75%.

3. The separating agent according to claim 1, wherein said calcium phosphate granules have an average granule size of 10 to 2000 μm.

4. The separating agent according to claim 1, wherein said calcium phosphate granules have a Ca/P ratio of 1.4 to 1.8.

5. The separating agent according to claim 4, wherein said calcium phosphate granules have a Ca/P ratio of 1.5 to 1.67.

6. A separating agent for separating at least one of cells and viruses comprising:
   a first element which comprises a polyvinyl acetal resin having an open cell structure, and an average pore size of 10 to 1000 μm; and
   a second element applied on said first element, said second element including a layer of porous calcium phosphate granules having an average granule size of 10 to 2000 μm.

7. The separating agent according to claim 6, further comprising, as a third element applied over said second element, polyvinyl acetal resin of having an open cell structure and an average pore size of 10 to 1000 μm, thereby sandwiching said second element between said first element and said third element.

8. The separating agent according to claim 6, wherein said polyvinyl acetal resin has an acetalization rate of 50 to 100%.

9. The separating agent according to claim 6, wherein said polyvinyl acetal resin has a porous sponge structure.

10. The separating agent according to claim 9, wherein said polyvinyl acetal resin comprises a spongy sheet.

11. The separating agent according to claim 6, wherein said calcium phosphate granules comprise:
    a first distribution and a second distribution of porous calcium phosphate granules having an open cell structure;
    said first distribution of porous calcium phosphate granules having a distribution of micropores ranging from 20 to 500 nm in average pore size; and
    said second distribution of porous calcium phosphate granules having a distribution of small pores ranging from 1 to 50 μm in average pore size.

12. The separating agent according to claim 11, wherein said calcium phosphate granules have a porosity of 10 to 75%.

13. The separating agent according to claim 6, wherein said calcium phosphate granules have a porosity of 10 to 75%.

14. The separating agent according to claim 6, wherein said calcium phosphate granules have a Ca/P ratio of 1.4 to 1.8.

15. The separating agent according to claim 14, wherein said calcium phosphate granules have a Ca/P ratio of 1.5 to 1.67.

16. A separator for separating at least one of cells and viruses comprising:
    a container;
    said container including therein a first distribution and a second distribution of porous calcium phosphate granules having an open cell structure;
    said first distribution of porous calcium phosphate granules having a distribution of micropores ranging from 20 to 500 nm in average pore size; and
    said second distribution of porous calcium phosphate granules having a distribution of small pores ranging from 1 to 50 μm in average pore size.

17. The separator according to claim 16, wherein said calcium phosphate granules have a porosity of 10 to 75%.

18. The separator according to claim 17, wherein said calcium phosphate granules have an average granule size of 10 to 2000 μm.

19. The separator according to claim 16, wherein said calcium phosphate granules have an average granule size of 10 to 2000 μm.

20. A separator for separating at least one of cells and viruses comprising:
    a container; and
    said container including therein (i) a first element which comprises a polyvinyl acetal resin having an open cell structure, and an average pore size of 10 to 1000 μm, and (ii) a second element applied on said first element, said second element including a layer of porous calcium phosphate granules having an average granule size of 10 to 2000 μm.

21. The separator according to claim 20, further comprising, as a third element applied over said second element, polyvinyl acetal resin of having an open cell structure and an average pore size of 10 to 1000 μm, thereby sandwiching said second element between said first element and said third element.

22. The separator according to claim 21, wherein said polyvinyl acetal resin has an acetalization rate of 50 to 100%.

23. The separator according to claim 21, wherein said polyvinyl acetal resin has a porous sponge structure.

24. The separator according to claim 20, wherein said calcium phosphate granules comprise:
   a first distribution and a second distribution of porous calcium phosphate granules having an open cell structure;
   said first distribution of porous calcium phosphate granules having a distribution of micropores ranging from 20 to 500 nm in average pore size; and
   said second distribution of porous calcium phosphate granules having a distribution of small pores ranging from 1 to 50 μm in average pore size.

25. The separator according to claim 20, wherein said calcium phosphate granules have a Ca/P ration of 1.4 to 1.8.

26. The separating agent according to claim 25, wherein said calcium phosphate granules have a Ca/P ratio of 1.5 to 1.67.

27. A method of separating at least one of cells and viruses comprising:
   passing a biological fluid containing at least one of cells and viruses through at least one column filled with a separating agent, wherein said separating agent comprises:
   a separating agent comprising a first distribution and a second distribution of porous calcium phosphate granules having an open cell structure, said first distribution of porous calcium phosphate granules having a distribution of micropores ranging from 20 to 500 nm in average pore size, and said second distribution of porous calcium phosphate granules having a distribution of small pores ranging from 1 to 50 μm in average pore size.

28. The method according to claim 27, wherein said biological fluid comprises blood, serum, urine, saliva or a suspension of at least one of cells and virus.

29. The method according to claim 28, wherein said separating agent further includes, as a third element applied over said second element, polyvinyl acetal resin having an open cell structure and an average pore size of 10 to 1000 μm, thereby sandwiching said second element between said first element and said third element.

30. The method according to claim 27, wherein said biological fluid comprises a diluted solution of blood, wherein the blood is treated with a blood coagulation inhibitor and diluted with a culturing solution to increase its volume by one through ten times.

31. A method of separating at least one of cells and viruses comprising:
   passing a biological fluid containing at least one of cells and viruses through at least one column filled with a separating agent, wherein said separating agent comprises:
   a separating agent comprising a first element which comprises a polyvinyl acetal resin having an open cell structure and an average pore size of 10 to 1000 μm, and a second element applied on said first element which includes a layer of porous calcium phosphate granules having an average granule size of 10 to 2000 μm.

32. The method according to claim 31, wherein said biological fluid comprises blood, serum, urine, saliva or a suspension of at least one of cells and virus.

33. The method according to claim 31, wherein said biological fluid comprises a diluted solution of blood, wherein the blood is treated with a blood coagulation inhibitor and diluted with a culturing solution to increase its volume by one through ten times.

34. A method of separating at least one of cells and viruses comprising:
   passing a biological fluid comprising a diluted solution of blood, wherein the blood is treated with a blood coagulation inhibitor and diluted with a culturing solution to increase its volume by one through ten times, through at least one column filled with a separating agent, wherein said separating agent comprises:
   a separating agent comprising a polyvinyl acetal resin having an open cell structure and an average pore size of 10 to 1000 μm.

* * * * *